United States Patent [19]

Schwartz

[11] Patent Number: 4,572,594
[45] Date of Patent: Feb. 25, 1986

[54] ARTHROSCOPY SUPPORT STAND

[76] Inventor: C. Bruce Schwartz, 6594 Mill Creek Rd., The Dalles, Oreg. 97058

[21] Appl. No.: 578,221

[22] Filed: Feb. 8, 1984

[51] Int. Cl.[4] .................................................. B01L 9/02
[52] U.S. Cl. ...................................... 312/209; 312/312
[58] Field of Search ...................... 248/647, 648, 123.1; 312/250, 209, 312

[56] References Cited

U.S. PATENT DOCUMENTS

| | | | |
|---|---|---|---|
| 3,143,803 | 8/1964 | Lunn | 312/312 |
| 3,165,367 | 4/1962 | Rose. | |
| 3,348,799 | 10/1967 | Junkel et al. | |
| 3,352,521 | 11/1967 | Tyler | 248/123.1 |
| 3,530,513 | 9/1970 | Maurer et al. | |
| 3,597,033 | 8/1971 | Slouka. | |
| 4,138,815 | 2/1979 | Williams et al. | |
| 4,418,969 | 12/1983 | Hettman | 312/250 |

FOREIGN PATENT DOCUMENTS

422256 4/1967 Switzerland.

*Primary Examiner*—William E. Lyddane
*Assistant Examiner*—Joseph Falk
*Attorney, Agent, or Firm*—Klarquist, Sparkman, Campbell, Leigh & Whinston

[57] ABSTRACT

And arthroscopy support stand is disclosed which contains, in a single movable unit, all of the apparatus needed to perform arthroscopic surgery. The stand comprises a wheel-mounted steel cabinet with brakes at the back of the cabinet for immobilizing it. The cabinet has shelves, open at the front, for supporting various arthroscopic surgery appliances. Mounted at the back of the cabinet are two upright, vertically telescoping fluid bag standards which can be lowered separately to change fluid supplies without interrupting the flow of fluid under pressure to the surgical site. A vertical support column is mounted at the front of the cabinet on a pair of vertically-spaced parallel horizontal arms. The arms are pivotally mounted at the middle of the cabinet so that the support column can be shifted back and forth across the front of the cabinet. The support column has a telescoping upper portion supporting a boom from which a television camera is suspended by an extensible cable counterweighted in the support column. A pair of articulated support arms are mounted one above the other on a lower portion of the support column for vertical and rotational movement to support a television monitor on one arm and an instrument tray on the other. The support arms can be moved up and down on the support column. The television monitor support arm is suspended via pulleys extending into the lower portion of the support column alongside the counterweight to connect under tension to a vertically-extensible coil spring positioned concentrically around the counterweight.

22 Claims, 10 Drawing Figures

ARTHROSCOPY SUPPORT STAND

BACKGROUND OF THE INVENTION

This invention relates generally to surgical operating room furniture and equipment and more particularly to apparatus for supporting arthroscopic surgery apparatus.

Arthroscopic surgery requires several pieces of equipment not required for other forms of surgery, including a pressurized saline fluid source, a television camera, a television signal generator, a television monitor, and several other electrical applicances. Heretofore, this equipment has been provided and arranged in the operating room in a rather haphazard fashion. A substantial amount of time is required to set up and take the equipment down each time it is to be used in a different operating room or to allow use of the operating room for a different kind of surgery. Typically, the equipment is arranged on whatever operating room furniture is available without regard to the convenience of use.

It is desirable to position the television monitor so that the surgeon can easily see it while working at the surgical site, but most common surgical furniture provides little flexibility in this regard. It is also desirable to be able to freely position the video camera for viewing the surgical site, but most available operating room equipment is ill-suited for this purpose.

Typically, an intravenous fluid standard is used to support a pair of elevated saline fluid bags. The fluid bags feed fluid via short tubes through a T-connector into a single conduit which is extended to the surgical site. When the bags are nearly empty, the standard must be lowered to change the bags. Lowering the bags reduces the fluid pressure in the conduit, allowing cloudy fluids and blood to enter the surgical site and thereby obsure the surgeon's view until fluid pressure is restored and the obscuring fluids are washed away. This disrupts and slows down the operation. Other drawbacks arise which vary from one arrangement to another of the arthroscopic surgical equipment.

In an attempt to unitize and more conveniently arrange arthroscopic surgical equipment, an arthroscopic surgical support stand has been proposed by Instrument Makar of Okemos, Mich., and is marketed under the brand name THE SURGI-CENTER. This support stand is intended to support in a single unit all of the special purpose apparatus required for arthroscopic-surgery. However, the manner in which such apparatus can be arranged on the stand is less than advantageous and the arrangement of the stand itself creates new problems that are preferably avoided. The stand is a gantry structure comprising two vertically-spaced shelves supported between a pair of wheeled legs. The legs are laterally spaced and the shelves are elongated so that the stand can straddle the operating table. An overhead video boom is connected to the shelves midway between the legs and extends vertically above the shelves for suspending a camera over the operating site. A saline fluid support column is mounted at each lateral end of the stand. In use, the television monitor and other equipment are placed on the shelves and the various wiring and tubing are extended downwardly from the standard to the operating site.

There are various drawbacks to this arrangement. The gantry is generally cumbersome to use and to store and does not support enough equipment. The most serious drawback is that, straddling the operating table and the patient, the stand obstructs access to the patient. Thus, it is not adaptable to surgical operation of joints other than the knee and ankle, such as to shoulders, elbows and hips. In case of an emergency, and upon completion of an operation, the support stand has to be wheeled lengthwise over the table, after detaching any wires and tubes extending down to the patient. In an emergency in which time is of the essence, the time required to disconnect and remove the unit can be critical. Mounting the television monitor on the top shelf of the stand is also a disadvantage, particularly if the surgeon is operating in a seated position. Adjacent electrical equipment can also interfere with operation of the monitor. Equipment positioned on the shelves over the patient is also difficult to reach without reaching across a sterile field and is not protected from saline fluid spills. Nothing in the stand supports surgical instruments conveniently for the surgeon and the gantry structure prevents use of a conventional Mayo tray. One saline fluid support column at a time is used for operating on one side or the other of the patient and the support columns are spaced too far apart to supply fluid to one surgical site from both support columns at the same time.

Outside the field of arthroscopic surgery, a variety of support apparatus or furniture is known, particularly for use in the field of dentistry. Swiss Patent. No. 422,256 discloses a dental cabinet which includes a sub-cabinet of drawers supported on an arm pivotally mounted in the cabinet base for lateral and rotational movement to position the sub-cabinet in easy reach of the dentist. U.S. Pat. No. 3,597,033 discloses a dental console mounted on wheels to facilitate positioning for convenient use by the dentist. U.S. Pat. No. 3,165,367 similarly discloses a wheeled artist's easel. U.S. Pat. Nos. 3,348,799 and 3,530,513 disclose articulated arm assemblies for supporting a dental bowl or dental instrument tray. U.S. Pat. No. 4,138,815 discloses a dental assistance console unit for supporting various dental instruments and a mobile work surface area for easy access by the user. However, none of these patents suggest how to arrange and support arthroscopic surgical equipment so as to overcome the above-described drawbacks of prior arrangements used in arthroscopic surgery.

Accordingly, the need remains for an arthroscopic support stand which overcomes the foregoing drawbacks.

SUMMARY OF THE INVENTION

One object of the invention is to improve upon prior systems and apparatus for arranging and supporting arthroscopic surgical equipment.

A second object is to arrange and support arthroscopic surgical equipment in a single unit which is compact, easily stored, and readily moved from one operating room to another.

Another object is to position arthroscopic surgical equipment for convenient use by the surgeon, regardless of the surgeon's operating position or the location of the joint, and to provide access to the equipment without reaching across a sterile field.

A further object of the invention is to provide easy access to all parts of the patient during arthroscopic surgery.

Yet another object is to enable the arthroscopic surgical equipment to be readily moved out of the way in case of an emergency and at the conclusion of surgery.

Other objects include electrically isolating the monitor from other electrical equipment, isolating the electrical equipment from saline spills, positioning surgical instruments within easy reach of the surgeon, and providing an uninterrupted flow of saline fluid to the surgical site.

An arthroscopic support stand in accordance with the invention comprises means defining a cabinet having a base, opposite sides, a front and shelves extending between the sides of the cabinet for supporting electrical equipment for use in performing arthroscopic surgery. A vertical support column having a lower portion and a telescoping upper portion is connected by mounting means to the cabinet and supported thereon in a predetermined lateral position in front of the shelves and at one side of the cabinet adjacent the patient and out of the way of the shelves to facilitate ready access to the electrical equipment in the cabinet. A boom means is pivotally mounted atop the upper portion of the support column for suspending a television camera above a predetermined portion of a surgical patient located adjacent one side of the cabinet. A television monitor support means on an articulated arm is pivotally mounted on the lower portion of the support column for supporting a television monitor operatively connected to the camera in position for viewing by a surgeon operating upon the predetermined portion of the patient.

Preferably, the boom includes a cable having an end extending from a distal end of the boom to suspend a television camera therefrom and extending within the boom and down into the support column for counterbalancing the weight of a camera suspended from the distal end of the cable and movable within the support column to facilitate changing the elevation of the camera. The monitor support means can include means movably connecting the support arm for vertical movement along the lower portion of the support column for selectively positioning the monitor at a predetermined position. A cable pulley means movably suspends the support arm upon the support column and extends downwardly inside the lower portion of the support column to connect to an upper end of a vertically-extensible spring means secured to the lower end of the support column for counterbalancing the weight of the monitor support means and television monitor. The coil spring and counterweight is concentrically arranged and sized so that the counterweight can descend within the coil spring.

The support stand can include an instrument tray mounted on a second support arm and means movably connecting the second arm to the lower portion of the support column below the monitor support arm for vertical movement to selectively position the instrument tray at a predetermined elevation. Means are provided for fixing the vertical position of the tray support arm, the support arm being articulated so that the tray can be readily positioned vertically and horizontally to facilitate access by the surgeon.

A pair of separate, vertical fluid bag standards can be positioned in closely-spaced relationship at the rear of the cabinet. Each standard has a lower portion connected to the cabinet and a telescoping upper portion for supporting a bag of fluid at an upper end of the standard. Means are provided for fixing the upper portions releasably in an extended position for gravity feeding fluid from the bags via fluid conduit means for supplying fluid under pressure to a surgical site and for lowering the standards independently of one another to change one bag at a time when empty while retaining one bag elevated to maintain fluid pressure in the fluid conduit means.

Preferably, the support column mounting means includes movable column support means for shifting the column laterally across the front of the cabinet to the opposite side thereof. Such means can be provided by a pair of vertically-spaced parallel, horizontal arms, each having one end pivotally connected between the sides and rearwardly of the front of the cabinet so that the support column can be swung from one side to the other across the front of the cabinet.

The foregoing and other objects, features and advantages of the invention become more readily apparent from the following detailed description of a preferred embodiment of the invention which proceeds with reference to the accompanying drawings.

DETAILED DESCRIPTION

Figures 1, 9:
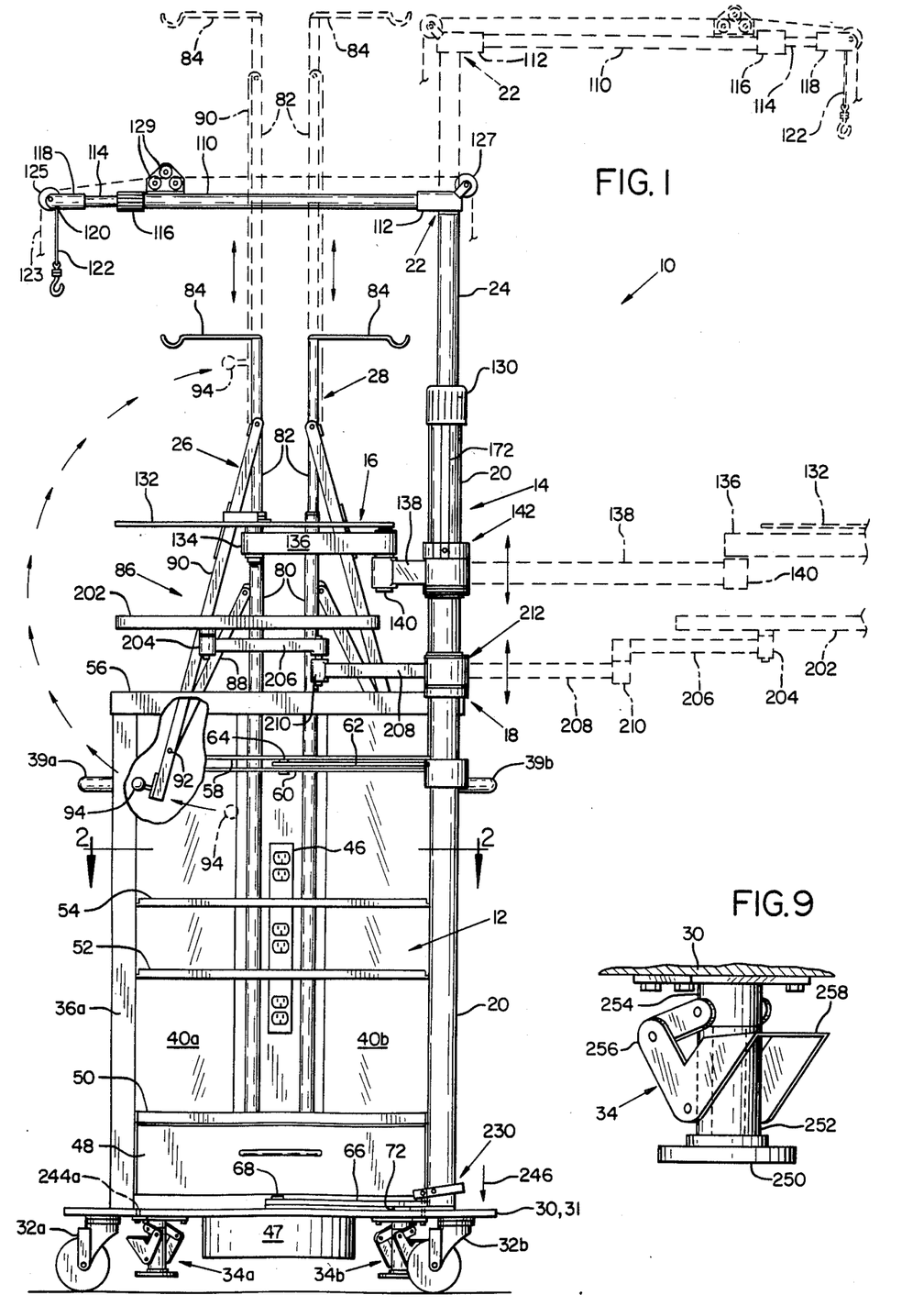
FIG. 1 is a front elevational view of an arthroscopic support stand in accordance with the invention, portions of the stand being shown in dashed lines in extended position for use during arthroscopic surgery.
FIG. 9 is a rear elevational view of the releasable brakes used in the support stand of FIG. 1.

Referring to FIG. 1, an arthroscopic support stand 10 in accordance with the invention includes a wheeled metal cabinet 12 and a vertical support column 14 mounted at the front of the cabinet. A pair of vertically-spaced support arm assemblies 16, 18 are mounted on a cylindrical tubular lower portion 20 of the support column. A boom assembly 22 is mounted on a telescoping cylindrical upper portion 24 of the support column. Mounted at the rear of the cabinet are a pair of vertically-extensible fluid support standards 26, 28.

Figures 2, 3, 4:
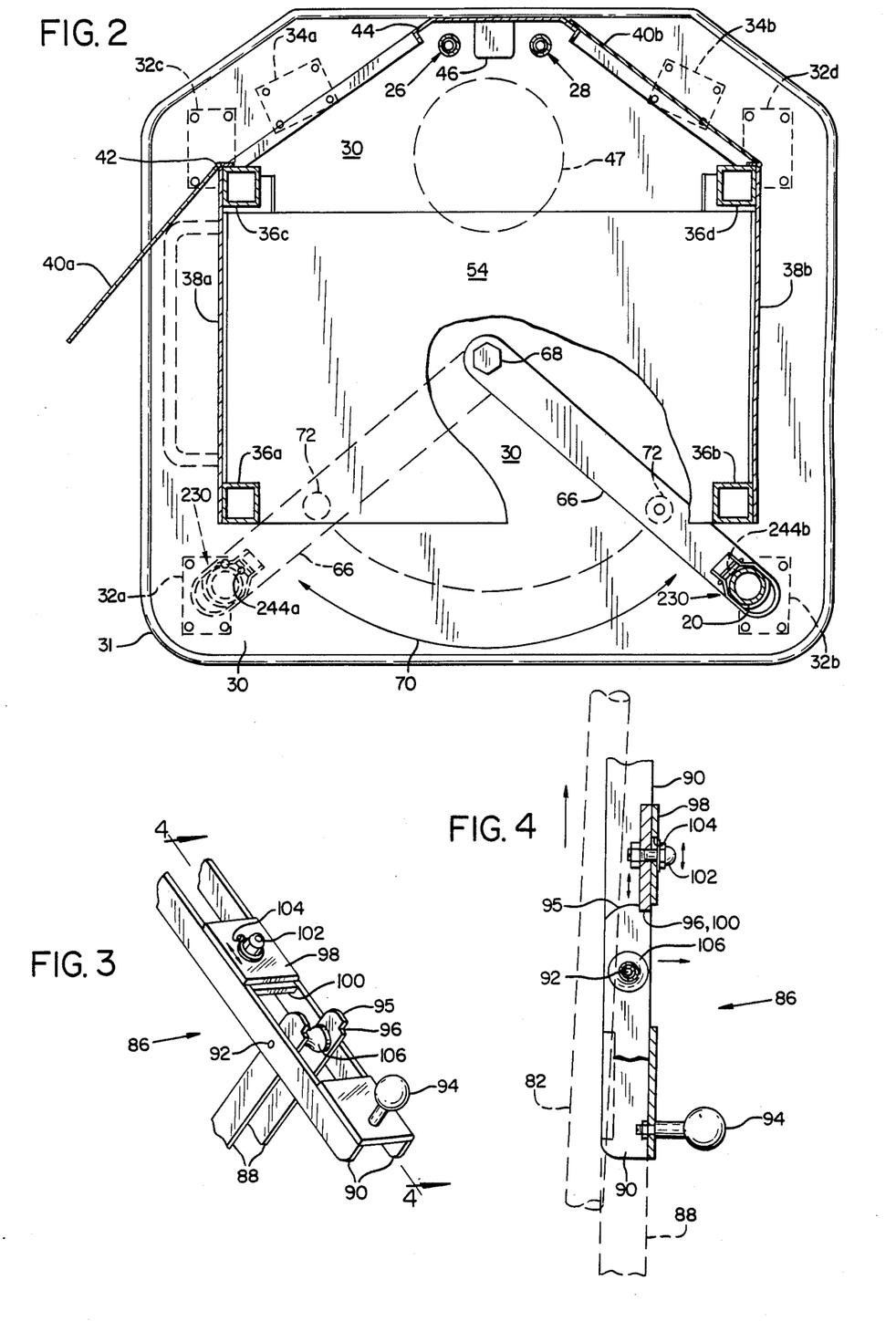
FIG. 2 is a cross-sectional view taken along lines 2—2 in FIG. 1, with a portion of the cabinet shelving cut away to show underlying structure.
FIG. 3 is a perspective view of a portion of the fluid standard raising assembly of the apparatus of FIG. 1.
FIG. 4 is a front elevational view of the raising assembly of FIG. 3 shown in an extended and locked position.

Cabinet 12, better seen in FIGS. 1 and 2 together, includes a flat base member 30 supported on four casters 32a–32d. The base member of a very thick metal, such as ½" thick steel plate, to counterbalance the weight of apparatus supported on support column 14 to facilitate extending the support arm assemblies without tipping the cabinet. A rubber bumper pad 31 extends around the base plate. Two brakes 34a, 34b, better seen in FIG. 9, are mounted under the rear portion of the base plate inwardly adjacent rear casters 32c, 32d, respectively.

The cabinet is framed by four vertical square tubular steel upright members 36a–36d rectangularly spaced rearwardly of support column 14 and inwardly of the casters 32. A pair of laterally-spaced sheet metal pads 38a, 38b define opposite sidewalls of the cabinet. A pair of U-shaped handle members 39a, 39b are mounted one on each side panel near the top of the cabinet. A pair of doors 40a, 40b are connected by hinges 42 to the sidewalls at the rear of the cabinet. At the back of the cabinet, a sheet metal panel 44 covers the lower portions of standards 26, 28 and lateral edges thereof serve as door jambs for closure of doors 40. An electrical power outlet box 46 is mounted inside the cabinet on panel 44 between support columns 26 and 28. A coil spring-loaded canister 47 mounted under plate 30 contains a retractable electric power cord (not shown) wired to outlet box 46. A drawer 48 is mounted in the bottom of the cabinet and spaced above base member 30 to provide a horizontal gap therebetween. Various shelves 50, 52, 54 are mounted in the cabinet, supported between upright members 36 which are slotted to adjust the elevation of the shelves. The cabinet has a top panel 56 whose outlines in plan view conform to the front, sides and back of the cabinet as shown in FIG. 2.

The support column is mounted on the front of cabinet 12 in a way that enables the column to be swung to one side or the other of the cabinet. A pair of rectangular horizontal plate members 58, 60 are spaced a short distance below the top of the cabinet and spaced closely together to provide a horizontal gap therebetween. An upper support arm 62, supporting column 14, is positioned in this gap and connected by a pivot 64 extending vertically between plates 58, 60 so as to be swung horizontally within the gap about the pivot. Similarly, a lower support arm 66 is connected by a pivot 68 to bottom plate 30 in the gap between the drawer 48 and the bottom plate. Pivots 64, 68 are centered between the sides of the cabinet on a common vertical axis. Connected to the radially outer ends of arms 62, 66, through lower tubular portion 20, support column 14 can be swung across the front of the cabinet as indicated by arrow 70 in FIG. 2. A low frictional support pad 72 is mounted on the underside of arm 66 for sliding along the upper surface of plate 30. Pad 72 is made of a low friction bearing material, such as ultra high molecular weight plastic.

The fluid bag standards 26, 28 are identical in construction and operation. Each standard includes a tubular lower portion 80 connected at its lower end to bottom plate 30 and extending vertically a distance of, for example, eighteen inches, above the top of the cabinet. A cylindrical upper portion 82 of each standard is received in portion 80 and is vertically extensible within such portion to raise and lower a hook 84, mounted at the top of the standard, for raising and lowering a fluid bag (not shown) suspended from the hook.

A single-action raising and lowering device 86, better seen in FIGS. 3 and 4, is used to elevate a saline fluid bag (not shown) on the upper portion of each standard. Device 86 comprises a first elongated member 88 pivotally connected to an outer lateral side of lower portion 80 and a second elongated member 90 pivotally connected to the center of upper portion 82. Referring to FIG. 3, member 88 comprises a pair of parallel flat members spaced apart and nested between two parallel spaced flat members forming member 90. Such members are interconnected by a pivot pin 92. A portion of member 90 extends past pivot 92 and carries a knob 94 which is grasped by the user when raising and lowering the standard. The ends 95 of members 88 adjacent pivot 92 are generally rounded and form to provide a notch 96 in a laterally outer corner thereof. A vertically slidable locking member 98 is mounted between members 90 above pivot 92 in position for engaging notches 96 in ends 95 of members 88. The locking member comprises a plate extending between two adjacent edges of members 90 and connected thereto. A plate member 100 is slidably supported beneath plate 98 by a bolt 102 in an elongated slot 104 extending lengthwise of members 90 to permit plate 100 to move lengthwise of such members. As the standard is raised, upon approaching a nearly fully-extended position, surfaces 95 cammingly engage the adjacent edge face of plate 100, raising it. Then, as the standard reaches maximum extension, plate 100 drops under the force of gravity into notches 96 to lock the standard in a fully-extended position. To unlock and lower the standard, bolt 102 is pushed upwardly and knob 94 is pulled away from the standard. A roller 106 mounted on pin 92 provides contact between a side of upper tubular portion 82 and the raising and lower device.

Referring back to FIG. 1, the camera boom 22 comprises an elongated horizontal tubular member 110 connected atop the upper portion 24 of support column 14 by a right angle joint 112 which is pivotable about a vertical axis. A tubular extension portion 114 is slidably received within arm 110 and secured in a desired position by means of a threaded locking collar 116. The boom terminates in a nose member 118 having an opening 120 on its underside through which a cable 122 extends for suspending a camera from the boom.

Figure 5:
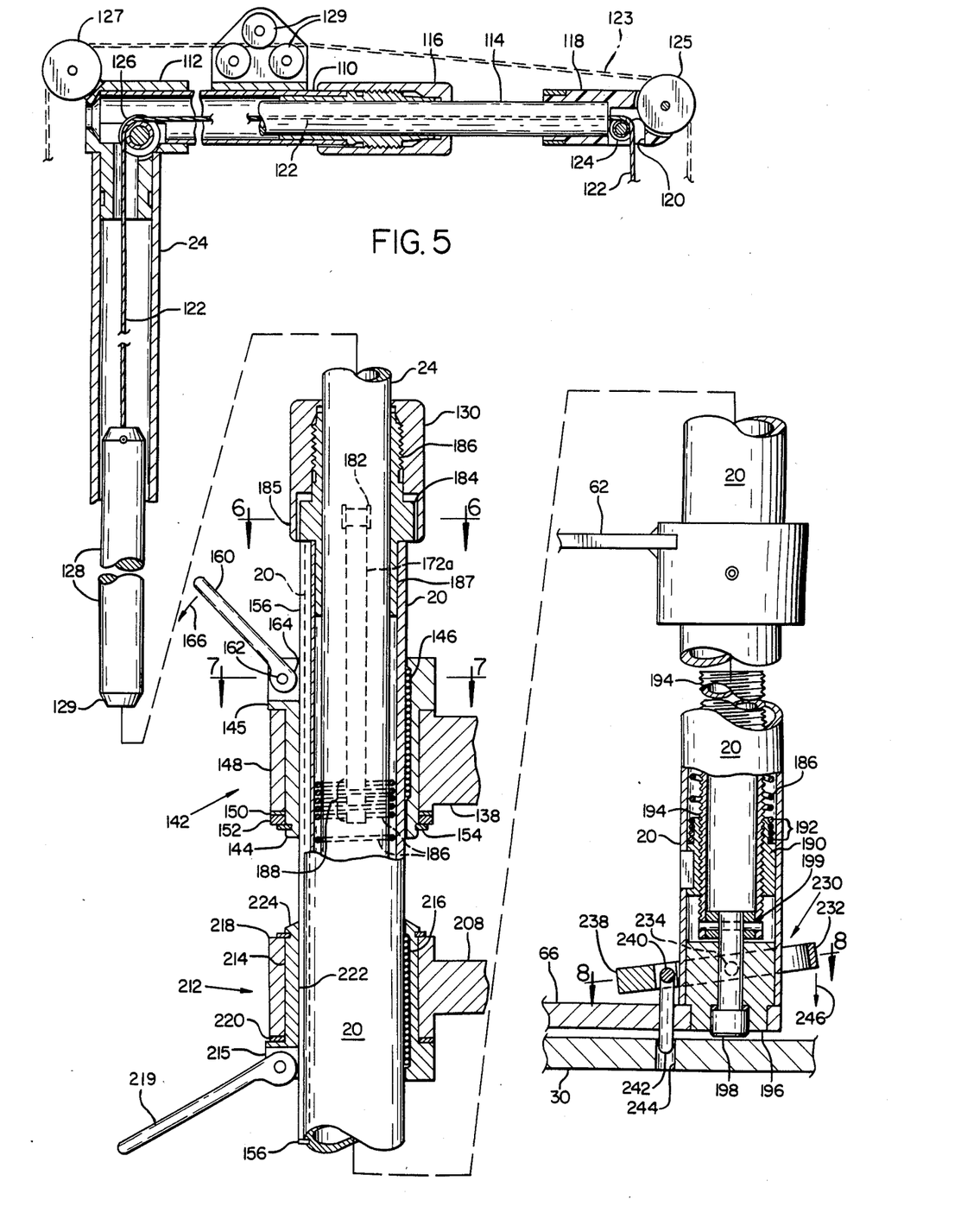
FIg. 5 is an enlarged fragmentary cross-sectional view of the support column and boom assembly of the stand of FIG. 1.

Referring to FIG. 5, the cable is supported inside nose 118, on a small sheave or roller 124. The cable extends lengthwise within tubular members 110, 114 to a second small sheave or roller 126 mounted inside joint 112. Cable 122 extends over the second roller and downward inside the upper portion 24 of support column 14. The cable is connected inside the support column to a counterweight 128 sized to counterbalance the weight of a television camera (not shown) suspended from the cable at the end of the boom. The counterweight is cylindrical and beveled at its ends 129. As shown in phantom lines in FIG. 1, the boom is positioned at any desired height by telescoping upper portions 24 within lower tube 20 and locking it in place be tightening a threaded, knurled locking collar 130 positioned at the upper end of lower portion 20.

Provision is also made to support a television signal cable 123 along the boom. A second sheave 125 is mounted in the end of nose 118 and protrudes outwardly and upwardly therefrom. A second sheave 127 is similarly mounted atop joint 112. A triangular array of guide rollers 129 is mounted atop member 110 near collar 116. Cable 123 extends downward along the support column to a video signal generator (not shown) in the cabinet. Alternatively, a lightweight tube camera (not shown) can be supported by rollers 125, 127, 129 without using cable 122.

Proceeding downward in FIGS. 1 and 5 along the support column, television monitor support arm assembly 16 comprises a tray 132 supported on a distal end of an articulated arm assembly through a pivot joint 134 rotatable upon a vertical axis. The arm assembly includes an arm outer portion 136 distally connected to the tray at joint 134 and proximately connected to an inner arm portion 138 at a joint 140 about which the two arm portions are relatively pivotable about a vertical axis.

The entire monitor support arm assembly is connected to the support column through a joint 142 which is both movable vertically on the column and pivotable about a vertical axis. Joint 142, best seen in FIGS. 5 and 7, comprises an annular sleeve 144 and integrally-connected radial flange 145 which surrounds tube 20 and is movable along it upon a plurality of radially-spaced sets of linear bearings 146. Arm 132 is provided with a cylindrical arm end 148 journaled on sleeve 144 and supported for rotation thereon by annular support bearing rings 150, 152. The bearing rings and arm end 148 are secured in place and held upwardly against flange 145 by an annular retaining ring 154 received in an annular groove at the base of member 144. A square key 156 extends vertically along a side of member 20 and protrudes outwardly into a complementary keyway 158 in sleeve and flange member 144, 145. A brake lever or cam lock 160 is mounted on a pivot bolt 162 in a side of flange 145. Lever 160 has a lobed cam head 164 positioned to engage the outer face of key 156. Cam head 164 is formed with an increasing radius proceeding downwardly around pin 162 so that, pushing the lever down as indicated by arrow 166 locks head 164 against key 156.

Figures 6, 7, 10:
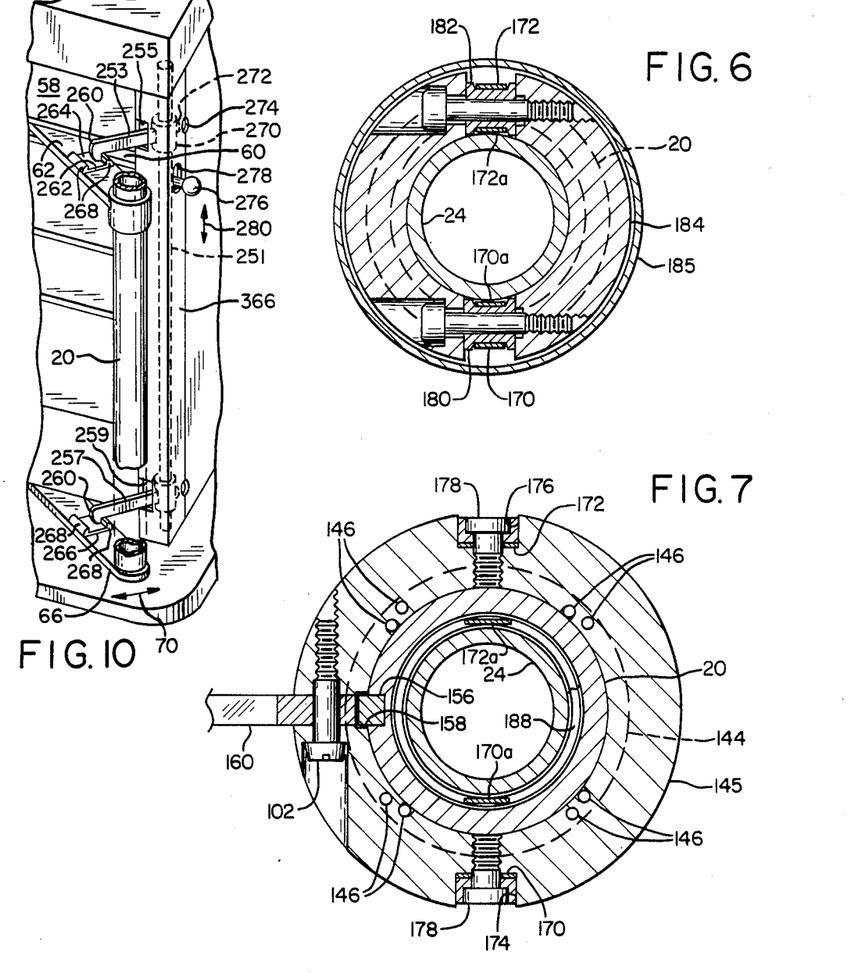
FIG. 6 is a cross-sectional view taken along lines 6—6 in FIG. 5.
FIG. 7 is a cross-sectional view taken along lines 7—7 in FIG. 5.
FIG. 10 is a fragmentary perspective view of a portion of the cabinet and support column of FIG. 1 showing a second form of column locking mechanism.

The weight of the monitor support arm assembly is counterbalanced to facilitate raising and lowering the monitor when the cam lock is released. Assembly 16 is supported through connector 142 by means of a pair of nylon straps 170, 172 extending upward along opposite outer sides of tube 20 to locking collar 130. Referring to FIG. 7, outer ends of straps 170, 172 are received in vertical slots 174, 176 in flange 145, to which they are secured by bolts 178. The nylon straps extend upward and inward over rollers 180, 182 located on opposite sides of tube 20. The rollers are mounted on an annular flange 184 integrally connected beneath the inner threaded portion 186 of a column locking assembly underlying collar 130. Flange 184, threaded portion 186, and a downwardly extending spacing sleeve 187 integrally form the inner portion of the column locking assembly. Flange 184 is supported on the upper end of lower tube 20 and, together with the rollers, is enclosed by a skirt 185 depending from collar 130. The upper tube 24 extends downwardly through the upper threaded portion 186. Upper tube 24 is spaced radially inward of the inside of lower tube 20 and centered therein by spacing sleeve 187. The inner ends 170a, 172a of straps 170, 172 extend downwardly within the annular space between tubes 20, 24 to a vertically-extensible coil spring 188 concentrically disposed within the annular space. The inner ends of the nylon straps are interwoven among the uppermost four or five coils of the spring on each side of tube 24.

Referring to the rightmost portion of FIG. 5, spring 188 extends downwardly to a vertically movable annular traveler 190. Member 190 is threaded at its upper end to receive four or five coils 192 of the spring and thereby secure the spring to traveler 190. Member 190 is internally threaded and received on an externally-threaded tubular member 194 concentrically positioned within lower tube 20. A plug 196 is fitted into the bottom of tube 20 and a rotatable tension adjustment shaft 198 extends upwardly through the plug to the bottom of threaded pipe 194, to which it is connected by pin 199. Rotation of shaft 198 causes the threaded tube to move member 190 up or down to alter the tension on the spring. The spring is sized to provide a force of 30-50 pounds at one foot extension.

Threaded tube 194 has the same inside and outside diameter as upper tube 24 of the support column and is only about one foot long, so that tube 24 can be lowered nearly to the bottom of lower tube 20. Tubes 24, 194 being concentrically positioned within tube 20, counterweight 128 can readily move up and down within them. The beveled ends 129 of the counterweight facilitate vertical passage between tubes 24 and 194. Being spaced radially outwardly of pipes 20, 24, 194 and the counterweight, spring 186 can move freely up and down around them.

Referring back to FIG. 1, an instrument tray 202 is mounted on an articulated arm assembly 18 connected to the support column through a joint 204 pivotable about a vertical axis. Like the monitor support arm, the instrument tray support arm assembly comprises an outer arm portion 206 and an inner arm portion 208 interconnected by pivot 210. A vertically-movable and rotatable joint 212, best seen in the center portion of FIG. 5, connects arm assembly 18 to support column 14. Joint 212 is generally similar to joint 142 except that it is inverted to position an annular flange portion 215 of sleeve member 214 beneath the journaled proximal end 218 of inner arm portion 208. Joint 212 also contains linear bearings 216 to facilitate vertical movement of the arm assembly on tube 20. A bearing ring 220 is sandwiched between journaled end portion 218 and flange 215 to facilitate rotation of the arm assembly about the support column. A retainer ring 224 is received in an annular groove in bearing member 214 atop end portion 218. The arm assembly is thus rotatable on a vertical axis about sleeve 214 and the sleeve is movable up and down on lower portion 20 of the support column. Key 156 extends downwardly along the side of tube 20 through a keyway 222 inside member 214, 215. As the instrument tray is relatively light, no counterbalancing arrangement is required. A cam-lock 219 on flange 215 engages key 156 releasably to retain the instrument tray support arm at whatever elevation it is placed.

Figure 8:
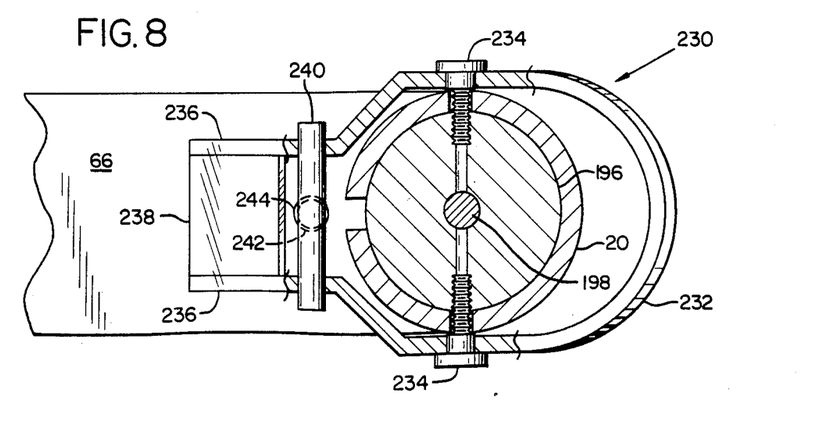
FIG. 8 is a cross-sectional view taken along lines 8—8 in FIG. 5.

Referring back to the rightmost portion of FIG. 5 and to FIG. 8, a locking assembly 230 is provided in the lower portion of support column 14 to lock the support column in a selected lateral position at the front of the cabinet. In one embodiment, the locking assembly comprises a generally U-shaped member 232 received on the lower end of lower tube 20 and pivotally connected to the tube along opposite sides thereof by a pair of horizontal pivot bolts 234. A weight 238 extends between the opposite ends 236 of the U-shaped member to bias ends 236 downward. A T-shaped member 240, having a depending central vertical leg or locking pin 242, is pivotally mounted between the opposite ends 236 of member 230. The bottom end of leg 242 is beveled or rounded to fit easily within a cylindrical vertical opening 244 in base plate 30. Preferably, two holes 242 are provided in the base plate, one on each side of the front of the cabinet as shown in FIG. 2. The holes are positioned such that the support column can be swung to one side or the other and locked in that position out of the way of the front of the cabinet and on the side of the cabinet nearer the operating table. Locking mechanism 230 is disengaged by the user pressing down on U-shaped member 232, as indicated in FIG. 5 by arrow 246, to raise leg 242 out of hole 244. The front of base plate 30 extends forwardly of the cabinet a distance such that leg 242 is supported on the base plate as the support column is swung across the front of the cabinet until it reaches a hole 244 on the opposite side of the cabinet. Then, under the influence of weight 238, the locking pin 242 drops into the hole to prevent further swinging of the support column.

An alternate column locking assembly is shown in FIG. 10. This embodiment is arranged to lock the support column arms 62, 66 directly against either front upright frame member 36a, 36b. A rod 25 is vertically centered in each front frame member. Two trip lock levers 253, 257 are mounted on each rod at an elevation adjacent arms 62, 66, respectively. The levers extend radially of the rod out of vertically elongated slots 255, 259 formed in the front inward corners of the upright members. A catch 262, 266 is mounted atop each arm 62, 66 in position to engage a downwardly-directed hook end 260 of each layer. The catches each have a central channel 264 defined by a pair of side walls 268 extending lengthwise of arms 62, 66. Each side wall has an upper face beveled or inclined downwardly away from the channel and the hook ends are similarly inclined to lift the levers over the side walls to catch the hooks in the notches. The levers are connected to the rod via slidable collars 270 and set screws 272 for adjusting the elevation of the levers relative to the catches. Openings 274 in the upright member enable access to the set screws. A radially extending handle member 276 is provided on the rod and protrudes through an elongated slot 278 in a side of member 36 for raising and lowering the rod. This action, indicated by arrow 280, disengages the levers from the catches and releases the support column.

Referring to FIG. 9, each brake 34 comprises a floor-engaging shoe 250 mounted on a vertically-movable shaft 252 received in a tube 254. The shoe is lowered by an over-center actuating linkage 256 by pushing down on an end 258 of such linkage. The brake is released by pushing up on end 258.

OPERATION

For use in arthroscopic surgery, support stand 10 is outfitted with the customary apparatus used for such surgery. A television camera is suspended from cable 122. A television monitor is positioned on tray 132. A television signal generator and other electronic equipment is positioned on the shelves of the cabinet and plugged into power outlet 46 at the back of the cabinet. A video signal cable 123 from the camera is positioned in the rollers along the camera boom and other cables are connected in conventional fashion to the various other pieces of equipment.

When not in use, such equipment is left assembled on the support stand. For storage, the upper portion of the support column, supporting the camera boom, is lowered and the camera boom is rotated over the cabinet as shown in FIG. 1. The monitor and instrument tray support arms are rotated to position them above the cabinet. The fluid bag standards are also lowered and the power cord is retracted into canister 47. In this position and with brakes 34 raised, support stand 10 is very compact. In can be easily wheeled through doorways from storage to an operating room and from one operating room to another without having to handle the various pieces of arthroscopic surgery equipment separately.

When the support stand is to be placed in use, it is wheeled alongside the operating table, whichever side is more convenient, and brakes 34 are set to immobilize the cabinet. Then, actuating brake lock 230 or 251, support column 14 is swung to the side of the cabinet adjacent the operating table. Next, a saline fluid bag (not shown) is mounted on each of hooks 84 and prepackaged, sterile tubing (not shown) is extended downwardly from each bag through a shutoff valve to a T-connector. A third tube or conduit (not shown) extends downwardly from the T-connector to a surgical site and, when the fluid bag standards are raised, provides fluid under pressure to the surgical site. The standards are raised by grasping knob 94 and moving it upwardly about member 88 until roller 92 is against upper standard portion 82, at which point lock 100 engages in notches 96.

Loosening locking collar 130, the camera boom is raised to a desired elevation and secured by retightening the locking collar. The boom is then rotated to a desired position and extended as necessary by loosening locking collar 116, extending end portion 114, and then retightening the locking collar. The television camera is then lowered to a desired elevation by pulling downwardly on cable 122 and is retained in such position by counterweight 128. The television monitor and instrument tray support arm assemblies 16, 18 are extended to convenient lateral positions and raised or lowered to elevations convenient to the surgeon and locked by cam locks 160, 219. The effort of raising the television monitor support assembly is made easier by spring 186 applying tension through nylon straps 170, 172 to mounting joint 142. The arthroscopic surgery apparatus on the stand can now be conveniently connected to the patient to commence surgery.

During surgery, it is preferable to supply saline fluid from one fluid bag at a time; the flow from the other bag being prevented by a valve in its outlet line. When the first bag is nearly emptied, the valve of the second bag can be opened and that of the first bag closed. Then, the first bag is lowered by releasing lock 100 and grasping knob 94 to controllably lower the standard supporting the first bag. The nearly empty bag is then replaced by a full bag of fluid, while the second bag continues to supply fluid under pressure to the surgical sight so that surgery can continue without interruption.

Should the surgeon need to change position during surgery, for example, from standing to sitting, support assemblies 16, 18 can readily be lowered on support column 14 to keep the instruments within reach and the television monitor within easy view of the surgeon. Similarly, if the surgeon changes positioned laterally, for example, to operate on the patient's other knee, the camera boom and instrument tray and monitor articulated support arms are readily extended to accommodate the change of position.

The equipment on the shelves in the cabinet at one side of the operating table is readily accessible without reaching across a sterile field. The electrical equipment is isolated from fluid spills and, enclosed within the metal cabinet, is electrically isolated from the television monitor to minimize interference. The electrical equipment in the cabinet is also cooled by air flowing by convection inwardly between the lower shelves 50, 52 upwardly behind the shelves, and forwardly between the upper shelves and plates 54, 56, 58, 60.

In case of an emergency, and upon the completion of surgery, the camera boom and support arm can be easily swung away from the operating table out of the way above the support stand. Since all of the connections are made to the patient at the front of the cabinet, these need not be disconnected to move the camera, monitor, or instrument tray out of the way.

The support stand and the apparatus which it supports are readily moved to another operating room and can be easily rearranged for use on the opposite side of an operating table from that where it was previously used. Locking member 230 is merely disengaged from the base member and the support column is swung across the front of the cabinet to the opposite side, as shown in FIG. 2, where it is relocked in position.

Having illustrated and described the principles of my invention in a preferred embodiment, it should be readily apparent to those skilled in the art that the invention may be modified in arrangement and detail without departing from such principles. I claim all modifications coming within the spirit and scope of the following claims.

I claim:

1. An arthroscopic support stand, comprising:
    means defining a cabinet having a base, opposite sides, a front, a top and shelves extending between the sides of the cabinet for supporting electrical equipment for use in performing arthroscopic surgery;
    a vertical support column having a lower portion extending above the top of the cabinet and a vertically telescoping upper portion received in the lower portion;
    mounting means for connecting the support column to the cabinet and supporting it thereon in a predetermined lateral position in front of the shelves and at one side of the cabinet adjacent a patient and out of the way of the shelves to facilitate ready access to the electrical equipment in the cabinet;
    a television monitor support means including an articulated arm pivotally mounted on the lower portion of the support column extending radially outward therefrom for supporting a television monitor, operatively connected to a television camera, in position above the cabinet top for viewing by a surgeon operating upon a predetermined portion of the patient;
    joint means movably connecting the monitor support arm to the lower portion of the support column for vertical movement along and rotation around the lower portion of the support column to selectively position the monitor at a predetermined elevation and radial position, and
    locking means for locking the joint means solely against said vertical movement and thereby fixing the vertical position of the monitor support means and monitor such that the monitor can be readily positioned vertically and rotationally in any selected position above the cabinet including over the patient for viewing by the surgeon.

2. An arthroscopic support stand according to claim 1 including a boom means pivotally mounted atop the upper portion of the support column for suspending a television camera above a predetermined portion of a surgical patient located adjacent one side of the cabinet; and vertical positioning means including a cable for supporting the camera and pulley sheaves, the pulley sheaves movably connecting the cable to the boom and extending the cable down the support column for setting the camera in a predetermined vertical position.

3. An arthroscopic support stand, comprising:
    means defining a cabinet for supporting electrical equipment for use in performing arthroscopic surgery;
    a vertical support column extending above the cabinet;
    mounting means for connecting the support column to the cabinet and supporting it thereon in a predetermined position in front of and at one side thereof;
    a television monitor support means including an articulated arm pivotally mounted on the support column and extending radially outward therefrom for supporting a television monitor in position above the cabinet for viewing by a surgeon operating upon a predetermined portion of a patient;
    first joint means movably connecting the monitor support arm to the support column for vertical movement along and rotation around the support column to selectively position the monitor at a predetermined elevation and radial position,
    locking means for locking the joint means solely against said vertical movement and thereby fixing the vertical position of the monitor support means and monitor such that the monitor can be readily positioned vertically and rotationally in any selected position above the cabinet including over the patient for viewing by the surgeon;
    an instrument tray support arm; and
    second joint means movably connecting the instrument tray support arm to the lower portion of the support column below the monitor support arm for vertical and rotational movement to selectively position an instrument tray at a predetermined elevation and radial position and means for fixing the vertical position of the tray support arm, the instrument tray support arm being articulated so that the tray can be readily positioned vertically and horizontally to facilitate access by the surgeon.

4. A support stand according to claim 1 in which the cabinet includes side walls, a back wall and an open front, the back wall being spaced rearwardly of the shelves for air to flow convectively through the cabinet to cool electrical equipment therein during operation of said equipment.

5. An arthroscopic support stand, comprising:
    means defining a cabinet having a base, opposite sides, a front and shelves extending between the sides of the cabinet for supporting electrical equipment for use in performing arthroscopic surgery;
    a vertical support column having a lower portion and a telescoping upper portion;
    mounting means for connecting the support column to the cabinet and supporting it thereon in a predetermined lateral position in front of the shelves and at one side of the cabinet adjacent the patient and out of the way of the shelves to facilitate ready access to the electrical equipment in the cabinet;
    a boom means pivotally mounted atop the upper portion of the support column for suspending a television camera above a predetermined portion of a surgical patient located adjacent one side of the cabinet, the support solumn including vertical positioning means movably connected to the boom for setting the camera in a predetermined vertical position; and
    a television monitor support means including an articulated arm pivotally mounted on the lower portion of the support column for supporting a television monitor operatively connected to the camera in position for viewing by a surgeon operating upon the predetermined portion of the patient;

the vertical positioning means including a cable, pulley means for conducting the cable within the boom downwardly into the support column, and means connected to the cable within the support column for fixing the position of the cable; the cable having an end extending from a distal end of the boom to suspend a television camera therefrom, to vertically position the camera.

6. An arthroscopic support stand, comprising:

means defining a cabinet having a base, opposite sides, a front and shelves extending between the sides of the cabinet for supporting electrical equipment for use in performing arthroscopic surgery;

a vertical support column having a lower portion and a telescoping upper portion;

mounting means for connecting the support column to the cabinet and supporting it thereon in a predetermined lateral position in front of the shelves and at one side of the cabinet adjacent the patient and out of the way of the shelves to facilitate ready access to the electrical equipment in the cabinet;

a boom means pivotally mounted atop the upper portion of the support column for suspending a television camera above a predetermined portion of a surgical patient located adjacent one side of the cabinet; and a television monitor support means including an articulated arm pivotally mounted on the lower portion of the support column for supporting a television monitor operatively connected to the camera in position for viewing by a surgeon operating upon the predetermined portion of the patient;

the support stand further including means movably connecting the monitor support arm for vertical movement along the lower portion of the support column to selectively position the monitor at a predetermined elevation and means for fixing the vertical position of the monitor support means and monitor such that the monitor can be readily moved up and down to facilitate viewing by the surgeon;

the fixing means including a pulley extending longitudinally of the support column and means within the support column connected to the pulley for counterbalancing the weight of the support means and monitor.

7. An arthroscopic support stand, comprising:

means defining a cabinet having a base, opposite sides, a front and shelves extending between the sides of the cabinet for supporting electrical equipment for use in performing arthrosopic surgery;

a vertical support column having a lower portion and a telescoping upper portion;

mounting means for connecting the support column to the cabinet and supporting it thereon in a predetermined lateral position in front of the shelves and at one side of the cabinet adjacent the patient and out of the way of the shelves to facilitate ready access to the electrical equipment in the cabinet;

a boom means pivotally mounted atop the upper portion of the support column for suspending a television camera above a predetermined portion of a surgical patient located adjacent one side of the cabinet; and a television monitor support means including an articulated arm pivotally mounted on the lower portion of the support column for supporting a television monitor operatively connected to the camera in position for viewing by a surgeon operating upon the predetermined portion of the patient;

the boom means including a cable having an end extending from a distal end of the boom to suspend a television camera therefrom and extending within the boom and down into the support column for counterbalancing the weight of a camera suspended from the distal end of the cable and movable within the support column to facilitate changing the elevation of the camera;

the monitor support means including means movably connecting the support arm for vertical movement along the lower portion of the support column for selectively positioning the monitor at a predetermined position, cable pulley means movably suspending the support arm upon the support column and extending downwardly inside the lower portion of the support column to connect to an upper end of a vertically-extensible spring means secured to the lower end of the support column for counterbalancing the weight of the monitor support means and television monitor; and the coil spring and camera counterweight being concentrically arranged and sized so that the counterweight can descend within the coil spring.

8. An arthroscopic support stand, comprising:

means defining a cabinet having a base, opposite sides, a front and shelves extending between the sides of the cabinet for supporting electrical equipment for use in performing arthroscopic surgery;

a vertical support column having a lower portion and a telescoping upper portion;

mounting means for connecting the support column to the cabinet and supporting it thereon in a predetermined lateral position in front of the shelves and at one side of the cabinet adjacent the patient and out of the way of the shelves to facilitate ready access to the electrical equipment in the cabinet;

a boom means pivotally mounted atop the upper portion of the support column for suspending a television camera above a predetermined portion of a surgical patient located adjacent one side of the cabinet;

is a television monitor support means including an articulated arm pivotally mounted on the lower portion of the support column for supporting a television monitor operatively connected to the camera in position for viewing by a surgeon operating upon the predetermined portion of the patient; and a pair of separate, vertical fluid bag standards positioned in closely-spaced relationship at the rear of the cabinet, each standard having a lower portion connected to the cabinet and telescoping upper portion for supporting a bag of fluid at an upper end of the stand, and means for fixing the upper portions releasably in an extended position for gravity feeding fluid from the bags via fluid conduit means for supplying fluid under pressure to a surgical site and for lowering the standards independently of one another to change one bag at a time when empty while retaining one bag elevated to maintain fluid pressure in the fluid conduit means.

9. An arthroscopic support stand, comprising:

means defining a cabinet having a base, opposite sides, a front and shelves extending between the sides of the cabinet for supporting electrical equipment for use in performing arthroscopic surgery;

a vertical support column having a lower portion and a telescoping upper portion;

mounting means for connecting the support column to the cabinet and supporting it thereon in a predetermined lateral position in front of the shelves and at one side of the cabinet adjacent the patient and out of the way of the shelves to facilitate ready access to the electrical equipment in the cabinet;

a boom means pivotally mounted atop the upper portion of the support column for suspending a television camera above a predetermined portion of a surgical patient located adjacent one side of the cabinet; and a television monitor support means including an articulated arm pivotally mounted on the lower portion of the support column for supporting a television monitor operatively connected to the camera in position for viewing by a surgeon operating upon the predetermined portion of the patient;

the support column mounting means including movable column support means for shifting the column laterally across the front of the cabinet to the opposite side thereof.

10. A support stand according to claim 9 in which the support column mounting means comprises a pair of vertically-spaced parallel, horizontal arms, each arm having one end pivotally connected to the cabinet at a position spaced between the sides and rearwardly of the front of the cabinet and each arm having a second end protruding forwardly of the cabinet with the support column connected thereto so that the support column can be swung from one side to the other across the front of the cabinet.

11. A support stand according to claim 9 in which the lower portion of the support column includes locking means for releasably engaging the cabinet to lock the support column in a selected lateral position at the front of the cabinet.

12. A support stand according to claim 11 in which the locking means includes first and second locking means for releasably engaging the cabinet at each front corner of the cabinet for locking the support column selectively at either corner.

13. A support stand according to claim 9 in which the base of the cabinet includes wheels for rolling the cabinet around and brake means positioned at the back of the cabinet for releasably locking the cabinet in position so that it cannot roll.

14. An arthroscopic support stand, comprising:

means defining a cabinet having a base, opposite sides, a front and shelves extending between the sides of the cabinet for supporting electrical equipment for use in performing arthroscopic surgery;

a vertical support column having a lower portion positioned adjacent the front of the cabinet;

movable column mounting means for connecting the support column to the cabinet and supporting it movably thereon, comprising a pair of vertically-spaced parallel, horizontal arms, each arm having one end pivotally connected to the cabinet at a position spaced between the sides and rearwardly of the front of the cabinet and each arm having a second end protruding forwardly of the cabinet with the lower portion of the support column connected thereto so that the support column can be swung laterally from one side of the cabinet to the opposite side thereof across the front of the cabinet for positioning the support column selectively at either front corner of the cabinet; and a television monitor support means including an articulated arm pivotally mounted on the lower portion of the support column for supporting a television monitor, operatively connected to a television camera, in a position extended laterally a distance from the cabinet and radially of the column for viewing by a surgeon operating upon the predetermined portion of the patient.

15. A support stand according to claim 14 including means movably connecting the monitor support arm for vertical movement along the lower portion of the support column to selectively position the monitor at a predetermined elevation and means for fixing the vertical position of the monitor support means and monitor such that the monitor can be readily moved up and down to facilitate viewing by the surgeon.

16. An arthroscopic support stand, comprising:

means defining a cabinet for supporting electrical equipment for use in performing arthroscopic surgery;

a vertical support column extending above the cabinet;

mounting means for connecting the support column to the cabinet and supporting it thereon in a predetermined position in front of and at one side thereof;

a television monitor support means including an articulated arm pivotally mounted on the support column and extending radially outward therefrom for supporting a television monitor in position above the cabinet for viewing by a surgeon operating upon a predetermined portion of a patient;

joint means movably connecting the monitor support arm to the support column for vertical movement along and rotation around the support column to selectively position the monitor at a predetermined elevation and radial position, and locking means for locking the joint means solely against said vertical movement and thereby fixing the vertical position of the monitor support means and monitor such that the monitor can be readily positioned vertically and rotationally in any selected position above the cabinet including over the patient for viewing by the surgeon;

the joint means including:

a first annular sleeve received on the support column and movable vertically and rotationally thereon;

a second annular sleeve received on the support column beneath the first sleeve and movable vertically on the column; and bearing means for supporting the first sleeve on the second sleeve for relative rotational movement;

the second sleeve including said locking means; and the articulated arm of the monitor support means being connected to the first sleeve.

17. A support stand according to claim 14 in which the support column includes a vertically adjustable upper portion and a boom means pivotally mounted atop the upper portion of the support column for suspending a television camera above a predetermined portion of a surgical patient located adjacent one side of the cabinet; and vertical positioning means including a cable and pulley sheaves movably connecting the cable to the boom and extending the cable down the support column for setting the camera in a predetermined vertical position.

18. An arthroscopic support stand, comprising:
means defining a cabinet having a base, opposite sides, a front and shelves extending between the sides of the cabinet for supporting electrical equipment for use in performing arthroscopic surgery;
a vertical support column having a lower portion and a telescoping upper portion;
mounting means for the support column comprising a pair of vertically-spaced parallel, horizontal arms, each arm having one end pivotally connected to the cabinet at a position spaced between the sides and rearwardly of the front of the cabinet and each arm having a second end protruding forwardly of the cabinet with the support column connected thereto so that the support column can be swung laterally from one side of the cabinet to the opposite side thereof across the front of the cabinet;
a television monitor support means including an articulated arm pivotally mounted on the lower portion of the support column for supporting a television monitor operatively connected to a television camera in a position extended a distance from the cabinet for viewing by a surgeon operating upon the predetermined portion of the patient; and
the cabinet base being weighted to counterbalance the weight of a television monitor on the support means when the arm is fully extended.

19. A support stand according to claim 18 including a boom pivotally connected atop the upper portion of the support column for extension of a cable down to the patient and pulley means for movably guiding the cable along the boom and down the support column.

20. An arthroscopic support stand, comprising:
means defining a cabinet having a base, opposite sides, a front and shelves extending between the sides of the cabinet for supporting electrical equipment for use in performing arthroscopic surgery;
a vertical support column having a lower portion and a telescoping upper portion;
mounting means for the support column comprising a pair of vertically-spaced parallel, horizontal arms, each arm having one end pivotally connected to the cabinet at a position spaced between the sides and rearwardly of the front of the cabinet and each arm having a second end protruding forwardly of the cabinet with the support column connected thereto so that the support column can be swung laterally from one side of the cabinet to the opposite side thereof across the front of the cabinet;
a television monitor support means including an articulated arm pivotally mounted on the lower portion of the support column for supporting a television monitor operatively connected to a television camera in a position extended a distance from the cabinet for viewing by a surgeon operating upon the predetermined portion of the patient; and
locking means including first and second locking means for releasably engaging the cabinet at each front corner of the cabinet for locking the support column selectively at either corner.

21. An arthroscopic support stand, comprising:
means defining a cabinet having a base, opposite sides, a front and shelves extending between the sides of the cabinet for supporting electrical equipment for use in performing arthroscopic surgery;
a vertical support column and mounting means for connecting the support column to the cabinet and supporting it thereon in a predetermined lateral position in front of the shelves and at one side of the cabinet adjacent the patient and out of the way of the shelves to facilitate ready access to the electrical equipment in the cabinet;
a first support means including an arm pivotally mounted on the support column for supporting a first arthroscopic surgical apparatus and laterally positioned for ready access by a surgeon operating upon the predetermined portion of the patient; and
a second support means pivotally mounted on the column for supporting a second arthroscopic surgical apparatus and laterally positionable in a predetermined location relative to the patient;
the second support means including vertically movable means including a counterweight extending downwardly into the support column for counterbalancing the weight of the second apparatus and movable vertically within the support column to facilitate changing the elevation of the second apparatus;
the first support means including means movably connecting the support arm to the support column for vertical movement therealong for selectively positioning the first apparatus at a predetermined elevation, cable pulley means movably suspending the first support means upon the support column and extending downwardly inside the lower portion of the support column to connect to an upper end of a vertically-extensible spring means secured to the lower end of the support column for counterbalancing the weight of the first support means and first appartus;
the coil spring and counterweight being concentrically arranged and sized so that the counterweight can descend freely within the coil spring.

22. An arthroscopic support stand, comprising:
means defining a cabinet having a base, opposite sides, a front and shelves extending between the sides of the cabinet for supporting electrical equipment for use in performing arthroscopic surgery;
a vertical support column having a lower portion and a telescoping upper portion;
mounting means for the support column comprising a pair of vertically-spaced parallel, horizontal arms, each arm having one end pivotally connected to the cabinet at a position spaced between the sides and rearwardly of the front of the cabinet and each arm having a second end protruding forwardly of the cabinet with the support column connected thereto so that the support column can be swung laterally from one side of the cabinet to the opposite side thereof across the front of the cabinet;
a television monitor support means including an articulated arm pivotally mounted on the lower portion of the support column for supporting a television monitor operatively connected to a television camera in a position extended a distance from the cabinet for viewing by a surgeon operating upon the predetermined portion of the patient; and
including a pair of separate, vertical fluid bag standards positioned in closely-spaced relationship at the rear of the cabinet, each standard having a lower portion connected to the cabinet and a telescoping upper portion for supporting a bag of fluid at an upper end of the stand, and means for fixing the upper portions releasably in an extended position for gravity feeding fluid from the bags via fluid conduit means for supplying fluid under pressure to a surgical site and for lowering the standards independently of one another to change one bag at a time when empty while retaining one bag elevated to maintain fluid pressure in the fluid conduit means.

* * * * *

UNITED STATES PATENT AND TRADEMARK OFFICE
CERTIFICATE OF CORRECTION

PATENT NO. : 4,572,594   Page 1 of 2
DATED : February 25, 1986
INVENTOR(S) : C. Bruce Schwartz It is certified that error appears in the above-identified patent and that said Letters Patent is hereby corrected as shown below:

In the abstract:

Line 1, "And" should be --An--;

In the specification and claims:

Column 1, line 13  "applicances" should be --appliances--;

line 38  "obsure" should be --obscure--;

line 49  "arthroscopic-" should be --arthroscopic--;

Column 2, line 27  "Patent." should be --Patent--;

Column 4, line 35  "FIg." should be --FIG.--;

Column 5, line 6  "pads" should be --panels--;

Column 6, line 3  "grapsed" should be --grasped--;

line 49  "be" should be --by--;

Column 8, line 60  "242" should be --244--;

Column 9, line 12  "25" should be --251--;

line 20  "layer" should be --lever--;

UNITED STATES PATENT AND TRADEMARK OFFICE
CERTIFICATE OF CORRECTION

PATENT NO. : 4,572,594

DATED : February 25, 1986

INVENTOR(S) : C. Bruce Schwartz

It is certified that error appears in the above-identified patent and that said Letters Patent is hereby corrected as shown below:

Column 10, line 45 "sight" should be --site--;

line 52 "positioned" should be --position--;

Column 12, line 40 "claim 1" should be --claim 14--;

line 63 "solumn" should be --column--;

Column 13, line 55 "arthrosopic" should be --arthroscopic--;

Column 14, line 48 delete "is"; and

Column 18, line 37 "appartus" should be --apparatus--.

Signed and Sealed this

Twenty-seventh Day of May 1986

[SEAL]

Attest:

DONALD J. QUIGG

Attesting Officer

Commissioner of Patents and Trademarks